(12) United States Patent
Fritz et al.

(10) Patent No.: US 6,518,032 B1
(45) Date of Patent: Feb. 11, 2003

(54) RAPID METHODS FOR IDENTIFYING MODIFIERS OF CELLULAR APOPTOSIS ACTIVITY

(75) Inventors: Lawrence C. Fritz, Rancho Santa Fe; Jose-Luis Diaz, Carlsbad; Robert C. Armstrong; Kevin J. Tomaselli, both of San Diego, all of CA (US)

(73) Assignee: IDUN Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/300,374

(22) Filed: Apr. 27, 1999

Related U.S. Application Data

(62) Division of application No. 08/869,553, filed on Jun. 5, 1997, now Pat. No. 6,270,980.

(51) Int. Cl.[7] .............................. C12Q 1/00; C12Q 1/02; C12Q 1/18; C12Q 1/37
(52) U.S. Cl. ........................... 435/7.2; 435/4; 435/7.21; 435/23; 435/24; 435/29; 435/32; 435/375; 435/377; 436/63
(58) Field of Search ............................. 435/4, 7.21, 23, 435/24, 29, 32, 375, 377, 7.2; 436/63

(56) References Cited

U.S. PATENT DOCUMENTS

| | | | |
|---|---|---|---|
| 5,620,888 A | 4/1997 | Tomei | 435/325 |
| 5,624,808 A | 4/1997 | Thompson et al. | 435/7.24 |
| 5,637,465 A | 6/1997 | Trauth | 435/7.1 |
| 5,783,186 A | 7/1998 | Arakawa et al. | 424/143.1 |
| 5,821,072 A | * 10/1998 | Schwartz et al. | 435/15 |
| 6,015,665 A | * 1/2000 | Dixit | 435/6 |
| 6,107,041 A | * 8/2000 | Korneluk et al. | 435/6 |

FOREIGN PATENT DOCUMENTS

| | | |
|---|---|---|
| WO | WO 95/27903 | 10/1995 |
| WO | WO 96/26280 | 8/1996 |
| WO | WO 96/35124 | 11/1996 |
| WO | WO 97/06182 | 2/1997 |
| WO | WO 97/08174 | 3/1997 |
| WO | WO 97/09617 | 3/1997 |
| WO | WO 97/10349 | 3/1997 |
| WO | WO 97/18313 | 5/1997 |
| WO | WO 98/13690 | 4/1998 |

OTHER PUBLICATIONS

Armstrong et al., "Fas–induced Activation of the Cell Death––related Protease CPP32 Is Inhibited by Bcl–2 and by ICE Family Protease Inhibitors," *The Journal of Biological Chemistry* 271(25):16850–16855, 1996.

Enari et al., "Apoptosis by a cytosolic extract from Fas–activated cells," *The EMBO Journal* 14(21): 5201–5208, 1995.

Hockenbery et al., "Bcl–2 is an inner mitochondrial membrane protein that blocks programmed cell death," *Nature* 348: 334–336, 1990.

Los et al., "Requirement of an ICE/CED–3 protease for Fas/APO–1–mediated apoptosis," *Nature* 375:81–83, 1995.

\* cited by examiner

*Primary Examiner*—David Saunders
(74) *Attorney, Agent, or Firm*—Seed Intellectual Property Law Group PLLC

(57) ABSTRACT

The invention provides a single-well, microscale method of determining the specific apoptotic activity of a cell. The method consists of contacting a cell population of about $1 \times 10^5$ cells for a time period of between about 30 minutes and 4 hours with a sufficient volume of medium containing an apoptotic specific diagnostic reagent and a diagnostic accessory reagent so as to cover the cell population, and determining the activity of the apoptotic specific diagnostic reagent. The invention also provides a method of identifying a compound which induces apoptosis. The invention further provides a rapid method of identifying a compound which inhibits apoptosis.

32 Claims, 3 Drawing Sheets

SEQUENCE LISTING

```
<160> NUMBER OF SEQ ID NOS: 4

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence:  Substrate
      analogue of caspase family member.  Apoptotic specific diagnostic
      reagent.
<221> NAME/KEY: MOD_RES
<222> LOCATION: (4)
<223> OTHER INFORMATION: Where Aspartic Acid has been modified with a
      aminomethylcoumarin which fluoresces after protease cleavage

<400> SEQUENCE: 1

Asp Glu Val Asp
  1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence:  Substrate
      analogue of caspase family member.  Apoptotic specific diagnostic
      reagent.
<221> NAME/KEY: MOD_RES
<222> LOCATION: (4)
<223> OTHER INFORMATION: Where Aspartic Acid has been modified with a
      aminomethylcoumarin which fluoresces after protease cleavage
```

-continued

```
<400> SEQUENCE: 2

Tyr Val Ala Asp
1

<210> SEQ ID NO 3
<211> LENGTH: 5
<212> TYPE: PRT
<213> ORGANISM: Unknown
<220> FEATURE:
<223> OTHER INFORMATION: Description of Unknown Organism:  Conserved
      pentapeptide sequence within active site of known caspases

<400> SEQUENCE: 3

Gln Ala Cys Arg Gly
1               5

<210> SEQ ID NO 4
<211> LENGTH: 5
<212> TYPE: PRT
<213> ORGANISM: Unknown
<220> FEATURE:
<223> OTHER INFORMATION: Description of Unknown Organism:  Conserved
      pentapeptide sequence within active site of known caspases

<400> SEQUENCE: 4

Gln Ala Cys Gly Gly
1               5
```

RAPID METHODS FOR IDENTIFYING MODIFIERS OF CELLULAR APOPTOSIS ACTIVITY

CROSS-REFERENCE TO RELATED APPLICATION

This application is a divisional application of U.S. patent application Ser. No.08/869,553, filed Jun. 5, 1997, now U.S. Pat. No. 6,270,980.

BACKGROUND OF TEE INVENTION

This invention relates to the biological process of programmed cell death and, more specifically to rapid methods of measuring apoptotic activity and of screening for compounds which modulate apoptosis.

Cells can die by at least two fundamentally different biological processes, One process, termed necrosis, refers to cell or tissue death which usually occurs as a result of massive physical or chemical insult. Necrosis is characterized, in part, by cell swelling organelle disintegration and the leakage of cell cytoplasm into the extracellular space and is generally considered to be a passive process.

The alternative process of cell death is known as apoptosis or programmed cell death. This mechanism of cell death in mammalian cells is characterized by a set of morphological and biochemical changes that reflect an active cell suicide. Apoptotic changes include cell shrinkage, nuclear chromatin condensation and margination, and DNA fragmentation. Biochemical events include the externalization of phosphatidyl serine and the activation of aspartate-specific cysteine proteases.

In regard to the latter biochemical event, proteases within the cysteine aspartic acid protease family, also known as the ICE/CED-3 family, are critical for effecting the process of apoptosis. These enzymes are cysteine proteases and exhibit substrate specificity for cleavage after an aspartic acid residue. Due to these characteristics, these enzymes are now referred to by the above term "cysteine aspartic acid proteases" or "caspases". During the apoptotic process, caspase activity is generated in cells and known inhibitors of the caspase family of proteases inhibit apoptosis.

Apoptosis is important clinically for several reasons. In the field of oncology, many of the clinically useful drugs kill tumor cells by inducing apoptosis. For example, cancer chemotherapeutic agents such as cisplatin, etoposide and taxol all induce apoptosis in target cells. In addition, a variety of pathological disease states can result from the failure of cells to undergo proper regulated apoptosis. For example, the failure to undergo apoptosis can lead to the pathological accumulation of self-reactive lymphocytes such as that occurring in many autoimmune diseases, and can also lead to the accumulation of virally infected cells and to the accumulation of hyperproliferative cells such as neoplastic or tumor cells. The development of efficacious compounds which are capable of specifically inducing apoptosis would therefore be of therapeutic value in the treatment of these pathological diseases states.

In contrast, the inhibition of apoptosis is also of clinical importance. For example, cells are thought to die by apoptosis in the brain and heart following stroke and myocardial infarction, respectively. Moreover, the inappropriate activation of apoptosis can also contribute to a variety of other pathological disease states including, for example, acquired immunodeficiency syndrome (AIDS), neurodegenerative diseases and ischemic injuries other than these listed above.

As apoptotic inducers are of benefit in the previously mentioned disease states, specific inhibitors of apoptosis would similarly be of therapeutic value in the treatment of these latter pathological disease states.

Drug discovery benefits from the use of efficient high throughput methods which can rapidly identify specific molecules that interact with the target of interest. The identification of compounds which specifically modulate the apoptotic pathway so far has been hindered by the lack of such methods. Available methods are either limited by the lack of specificity and/or efficiency. For example, most anti-cancer drugs are screened for their ability to kill cells and therefore will identify compounds that induce both necrosis or apoptosis. Moreover, many of these methods are often cumbersome in that they require assessment of cell viability and take days to perform.

Attempts have been made to create methods that are specific for apoptosis. For example, the amount of DNA degradation induced in a cell population has been used for a measurement of apoptosis. However, DNA degradation is a relatively late step in the apoptotic process. Moreover, DNA degradation is not truly specific for apoptosis since DNA eventually becomes degraded in necrotic cells too.

Other methods currently employed use metabolic determinations as an attempt to measure apoptosis in a relatively shorter time frame. For example, cells undergoing apoptosis show impaired mitochondrial function which can be measured using dyes such as alamar blue or by colourimetric assays such as reduction of MTT (3-(4.5-dimethyl) thiazol-2-yl-2,5-diphenyl tetrazolium bromide) to formazan. However, impaired mitochondrial function is not specific for apoptosis as it is also a characteristic exhibited by necrotic cells.

There has been one method described where apoptotic measurements appear specific and are conducted in relatively short time periods. For example, the successful measurement of caspase activity by measuring the fluorescent cleavage product of the CPP32 substrate analog DEVD-AMC has been reported (Armstrong et al. *J. Biol. Chem.* 271:16850–16855 (1996)). However, this method required separate preparations of the cell lysate and reaction mixture as well as additional manipulations, including sample washing in the assay procedure. In addition to the extra time required to perform these additional manipulations, this method could not be performed in a single step due to the requirement for separate preparation of lysate and reaction mixture. Therefore, regarding high throughput assays for apoptosis, what benefit might have been gained in specificity was lost due the inefficiencies incurred in order to measure the caspase activity.

Another method specific for apoptosis has been reported where separate preparations of cell lysate and reaction mixture has not been required (Los et al. *Nature* 375:81–83 (1995)). This method similarly determined the caspase activity following induction of apoptosis by measuring the cleavage product of an ICE substrate analogue. Separate preparation of samples and reaction was avoided due to the use of a detergent which does not completely lyse the cells. However, the incomplete solubilization of cellular components can result in decreased sensitivity of the method. Moreover, the detection of substrate cleavage was performed by a separate procedure and, as with the method of Armstrong et al. above, similarly required additional manipulations and steps which lengthened the time period for the procedure.

Thus, there exists a need for rapid and efficient methods to identify compounds which can specifically modulate the apoptotic pathway for the therapeutic treatment of human diseases. The present invention satisfies this need and provides related advantages as well.

SUMMARY OF THE INVENTION

The invention provides a single-well, microscale method of determining the specific apoptotic activity of a cell. The method consists of contacting a cell population of about $1 \times 10^5$ cells for a time period of between about 30 minutes and 4 hours with a sufficient volume of medium containing an apoptotis-specific diagnostic reagent and a diagnostic accessory reagent so as to cover the cell population, and determining the activity of the apoptotis-specific diagnostic reagent. The invention also provides a method of identifying a compound which induces apoptosis. The method consists of (a) providing a cell over-expressing a cell survival polypeptide at a level which is sufficient to prevent the induction of apoptosis; (b) treating the cell over-expressing the cell survival polypeptide with a direct stimulus of the cell death pathway; (c) adding a compound to be tested for apoptotic inducing activity, and (d) determining cellular apoptotic activity, the presence of which is indicative of the compound being an apoptotic inducer. The invention further provides a rapid method of identifying a compound which inhibits apoptosis. The method consists of (a) separately contacting a plurality of cell populations with a different compound to be tested for apoptotic inhibiting activity; (b) incubating the cells with a direct stimulus of the cell death pathway for a period of between about 2 minutes to 3 hours, and (c) measuring the specific apoptotic activity of the cells.

BRIEF DESCRIPTION OF THE DRAWINGS

FIG. 1 shows a comparison of the single-well method of measuring specific apoptotic activity with a method requiring additional washing procedures.

FIG. 2 shows the induced caspase activity measured at different time points following treatment with a range of anti-Fas antibody concentrations.

DETAILED DESCRIPTION OF THE INVENTION

Figure 1A:
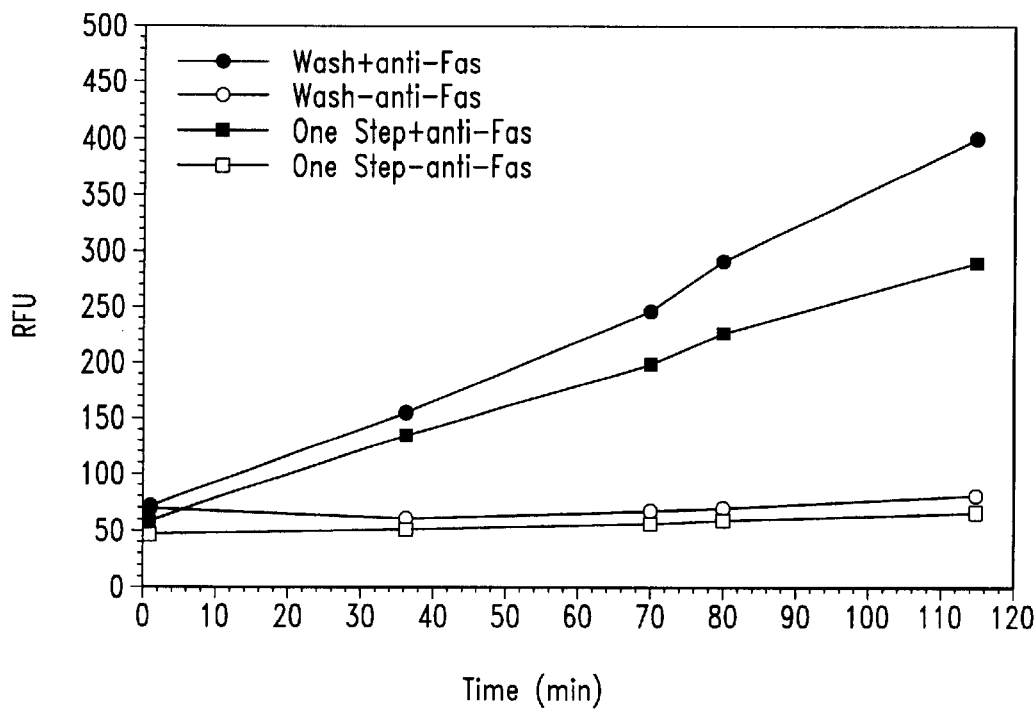
FIG. 1A shows the caspase activity induced in neo-transfected Jurkat cells in the presence (closed symbols) or absence (open symbols) of anti-Fas antibody.

This invention is directed to a novel method for the rapid and efficient measurement of apoptosis. The method is advantageous in that it distinguishes apoptosis from other forms of cell death and can be performed in a single step and on a small scale analysis. Moreover, the method is rapid in that it can be performed in a time period of between about 30 minutes and 4 hours. These advantages allow for the high throughput screening of a large number of samples with a specificity and time period not achieved before with previous methods known in the art. The method distinguishes apoptosis from other forms of cell death in that it measures the activity of cysteine aspartic acid proteases or other specific indicators of apoptosis. Therefore, the method can be advantageously used for the specific identification of inducers of apoptosis such as compounds that inhibit the function of Bcl-2.

In one embodiment, the invention is directed to a method of measuring apoptosis where a single buffer is added which contains a lysis agent and a detectable substrate for one or more aspartate specific cysteine proteases. A specific example of a detectable substrate is the peptide analogue DEVD-AMD (SEQ ID NO:1) which fluoresces after protease cleavage. Simultaneous lysis with substrate allows for the rapid measurement of aspartate specific cysteine protease activity without the necessity for washes or other transfer of reagents.

In another embodiment, the invention is directed to a method for identifying compounds which induce apoptosis. The method employs the measurement of induced cysteine aspartic acid protease activity in a cell line that expresses the Fas antigen and has been engineered to overexpress the cell survival polypeptide Bcl-2 and which has been treated with anti-Fas antibody. In a normal unengineered cell line, treatment with the anti-Fas antibody causes rapid apoptosis. However, in the engineered cell line apoptotic progression is blocked due to the continued presence of Bcl-2. Compounds that induce apoptosis are identified by incubating them with the engineered cell line that has also been incubated with anti-Fas antibody and then measuring apoptosis using the method described above. Due to the overexpression of Bcl-2, this method for identifying inducers of apoptosis will identify compounds that either inhibit the function of Bcl-2, or that stimulate the cell death pathway downstream of the Bcl-2 blockade. Moreover, since the engineered cells are treated with the pro-apoptotic anti-Fas antibody, these cells are primed for programmed cell death so that there is little or no lag time once the cells are treated with a positive apoptotic inducer. This priming of the cells provides additional sensitivity and speed for identifying apoptotic inducers. The priming for cell death can be provided by other pro-apoptotic stimuli including but not limited to, staurosporine, TNF and TNF plus cycloheximide.

In another embodiment, the invention is directed to a method of identifying inhibitors of apoptosis. This method also utilizes the single-step method described above, however, the indicator cell line does not require the overexpression of a cell survival polypeptide. Instead, the cells are first incubated with a compound to be tested for inhibitory activity and then treated with an direct stimulus of apoptosis such as anti-Fas antibody. In the absence inhibitory compounds, cells subsequently treated with anti-Fas antibody undergo apoptosis and exhibit a rapid induction of aspartate specific cysteine protease activity. In contrast, positive compounds inhibit the emergence of protease activity compared to control samples.

As used herein, the term "apoptosis" is intended to mean the physiological process known as programmed cell death. This process is a morphologically and biochemically distinct form of cell death that regulates cell turnover under normal physiological conditions. The morphological features include an orchestrated sequence of changes which include cell shrinkage, chromatin condensation, nuclear segmentation and eventual cellular disintegration into discrete membrane-bound apoptotic bodies. The biochemical features include, for example, internucleosomal cleavage of cellular DNA and the activation of ICE/Ced-3 family of proteases. The term "apoptosis" is used here synonymously with the phrase "programmed cell death." These terms are intended to be consistent with their use as they are known and used by those skilled in the art.

As used herein, the term "single-well" when used in reference to an apoptotic assay method is intended to mean that all actions, processes, or measures taken to achieve the determination of specific apoptotic activity are performed without the need for intermediary processing steps that require the cells to be moved from one well or vessel to another. Such intermediary processing steps can include, for example, cell harvesting; washing steps; purification steps; separation steps; exchange of additional buffers or reagents; media, reagent or lysate transfer; or, sample transfer or processing for analysis. The term includes, however, the addition or mixing of other buffers or reagents. Thus, the term "single-well" is intended to mean that the method can be performed by adding to a cell sample all reagents necessary to determine the specific apoptotic activity following an appropriate time of incubation. The addition of such reagents can be performed in a single step or they can be added sequentially. Measurement of specific apoptic activity therefore occurs without further processing or transfer of the sample. The term single-well is also intended to include scalable formats and automated procedures.

As used herein, the term "microscale" is intended to mean that the method can be performed on a scale measured in microliter ($\mu$l) or sub-microliter volumes and whereby many sample measurements can be made in parallel in, for example, multi-well plates. Such a scale is in contrast to milliters (ml) and to procedures not amenable to a multi-well format. A specific example of a multi-well format is a 96-well ELISA plate. The microscale measurable volumes are between about 1 and 200 $\mu$l, more preferably between about 30 and 125 $\mu$l, and preferably about 100 $\mu$l. Thus, a microscale method can be entirely performed, for example, in a microwell plate format such as a 96 well or other multiwell sample format.

As used herein, the term "specific apoptotic activity" is intended to mean cellular activity specifically due to the activation of the programmed cell death pathway. Programmed cell death is effected and regulated by a variety of molecules including the Bcl-2 and Bax polypeptides as well as the activation of members of the ICE/Ced3-family of cysteine aspartic acid proteases (caspases). Thus, cellular activity specifically due to the activation of the programmed cell death pathway is intended to mean the activity of molecules, including the above families of molecules, which regulate or participate in the apoptosis pathway and whose activity correlates with the appearance of apoptosis in these cells.

As used herein, the term "direct stimulus" when used in reference to the cell death pathway is intended to mean an agent that increases the specific apoptotic activity of a cell. Specific examples of direct stimuli include, for example, Fas ligand, anti-fas antibody, staurosporine, ultraviolet (UV) and gamma irradiation. Other direct stimuli exist and are known by those skilled in the art. Thus, a direct stimulus of apoptosis is an agent which increases the molecular activity of the above-described families of molecules which enhance or participate in apoptosis.

As used herein, the term "apoptotic specific diagnostic reagent" or "diagnostic reagent" is intended to mean a reagent which specifically measures or can be made to specifically measure the specific apoptotic activity of a cell. Such reagents include, for example, the measurement of caspase activity. Moreover, such measurements can be either direct or indirect. Apoptotic specific diagnostic reagents can include substrate analogues for caspase family members which fluoresce upon cleavage. Specific examples of such substrate analogues include, for example, ZEVD-AMC, YVAD-AMC (SEQ ID NO:2) and DEVD-AMC (SEQ ID NO:3) (carbobenzoxy-Glu-Val-Asp-aminomethylcoumarin, Tyr-Val-Ala-Asp-AMC and Asp-Glu-Val-Asp-AMC, respectively).

Reagents other than those which measure the binding or activity of cell survival or cell death polypeptides are similarly included within the definition of the term so long as such reagents can specifically measure, or be made to specifically measure apoptotic events. An example of such an apoptotic specific diagnostic reagent is the phospholipid binding polypeptide Annexin V. This reagent binds phosphatidylserine in a calcium dependent manner. Specificity of phosphatidylserine as a measure for apoptotic cells is due to the fact that this lipid is primarily found on the inner surface of a cell membrane but is translocated to the outer surface upon cell death. Its use in conjunction with a viability stain can provide specificity for apoptotic mediated cell death. Thus, the measurement of phosphatidylserine on the outer membrane surface can be used as an apoptotic specific diagnostic reagent. Other specific indicators of apoptosis exist and are known to those skilled in the art. Such other specific indicators are intended to be include within the definition of the term as defined and used herein.

As used herein, the term "diagnostic accessory reagent" or "accessory reagent" is intended to mean an agent that is required for the apoptotic specific diagnostic reagent to function. The agent can be a single ion, an organic or inorganic molecule, a macromolecule or any combination thereof. The requirement for function of the diagnostic reagent can be biochemical or physical. A specific example of a biochemical requirement is found with the case of Annexin V where calcium is necessary for phospholipid binding. A physical requirement for an accessory reagent is in the case where caspase activity is measured. In order to measure caspase activity, either the cell has to be lysed or the substrate analogue has to permeate the membrane. The accessory reagent would facilitate such a lysis or crossing of the membrane. Specific examples of such accessory reagents would be an agent which is capable of lysing the cell or disintegrating the cell membrane, or alternatively, an agent which punctures holes in the membrane to allow for molecules and macromolecules to cross the membrane. Such agents are known to those skilled in the art and are intended to be within the scope of the definition as it is used herein.

The term "lysis reagent" as it is used herein is therefore intended to mean a reagent which is capable of causing the dissolution or destruction of cellular membrane integrity. Such reagents generally include, for example, detergents such as SDS, NP-40 and triton, however, lysis reagents other than detergents are also included within the definition so long as such reagents do not interfere with the cellular apoptotic activity and detection using an apoptotic specific diagnostic reagent. Additionally, the meaning of the term is also intended to include detergents or other reagents which do not result in cellular destruction, but instead, are capable of permeabilizing the membrane and allowing entry of the diagnostic reagent. A specific example, of such a lysis reagent includes digitonin.

As used herein, the term "compound" when used in reference to an agent capable of inducing or inhibiting apoptosis is intended to mean a molecule able to modulate the specific apoptotic activity of a cell. Such a molecule can include small organic or inorganic molecules as well as large macromolecules. Specific examples of small molecules include etoposide and carbobenzoxy-Val-Ala-Asp-fluoromethylketone. Examples of macromolecules which are able to modulate the specific apoptotic activity of a cell include peptides, polypeptides, proteins, nucleic acid, carbohydrate and lipid. Functional or structural analogues or mimics of such compounds which exhibit substantially the same activation or inhibition activity are also included within the meaning of the term as used herein. The type, size or shape of the molecule is not important so long as the molecules can either induce or inhibit the specific apoptotic activity of a cell.

As used herein, the term "cell survival polypeptide" is intended to mean a peptide, polypeptide or protein that is capable of inhibiting the specific apoptotic activity of a cell. Cell survival polypeptides includes those polypeptides which directly regulate the programmed cell death pathway such as Bcl-2, Bcl-xL, Mcl-1 and the ElB-19K protein of adenovirus as well as those which indirectly regulate the programmed cell death pathway.

The meaning of the term "cell survival polypeptide" also includes functional fragments so long as they have the ability to inhibit the specific apoptotic activity of a cell. The term is also intended to include polypeptides that include, for example, modified forms of naturally occurring amino acids such as D-steroisomers, non-naturally occurring amino acids, amino acid analogues and structural mimics so long as such polypeptides retain functional activity as defined above.

As used herein, the term "overexpressing" when used in reference to the level of a cell survival polypeptide is intended to mean an increased accumulation of the cell survival polypeptide in the overexpressing cells compared to their levels in counterpart normal cells. Overexpression can be achieved by natural biological phenomenon as well as by specific modifications as is the case with genetically engineered cells. Overexpression also includes the achievement of an increase in cell survival polypeptide by both endogenous or exogenous mechanisms. Overexpression by natural phenomenon can result by, for example, a mutation which increases expression, processing, transport, translation or stability of the RNA an well an mutations which result in increased stability or decreased degradation of the polypeptide. Such examples of increased expression levels are also examples of endogenous mechanisms of overexpression. A specific example of a natural biologic phenomenon which results in overexpression by exogenous mechanisms is the adjacent integration of a retrovirus. Overexpression by specific modification can be achieved by, for example, the use of recombinant methods known in the art to construct and overexpress stably or transiently a cell survival polypeptide in a compatible vector-host system.

As used herein, the term "cell death polypeptide" is intended to mean a peptide, polypeptide, or protein that is capable of increasing or inducing the specific apoptotic activity of a cell. Cell death polypeptides includes those polypeptides which directly regulate the programmed cell death pathway such as Bax, Bad, Bcl-xS, Bak, and Bik as well as those which indirectly regulate the programmed cell death pathway. Cell death polypeptides also includes, for example, ICE/Ced3-family of caspases since such caspases can induce programmed cell death.

The meaning of the term "cell death polypeptide" also includes functional fragments so long as they have the ability to enhance or induce the specific apoptotic activity of a cell. As with functional fragments of the counterpart cell survival polypeptides, the term is also intended to include polypeptides that include, for example, modified forms of naturally occurring amino acids such as D-steroisomers, non-naturally occurring amino acids, amino acid analogues and structural mimics so long as such polypeptides retain functional activity as defined above.

As used herein, the term "aspartate specific cysteine protease" or "caspase" is intended to mean those family of proteases which are related genetically to the C. elegans ced-3 gene product and includes, for example, human ICE (interleukin-1-β converting enzyme), ICH-$1_L$, CPP32, Mch2, Mch3, Mch4, Mch5 Mch6, ICH-2 and ICE$_{rel}$-III. In addition to the shared homology to Ced3, the known caspases also share the following characteristics: 1) they exhibit cysteine protege activity with specificity for substrate cleavage at Asp-x bonds, 2) contain a conserved pentapeptide sequence (QACRG [SEQ ID NO:3], QACGG [SEQ ID NO:4] or a related sequence) within the active site and 3) are synthesized as proenzymes that require proteolytic cleavage at specific aspartate residues for activation of protease activity. Although these proteases are defined herein as cell death polypeptides, several alternative structural forms of caspases exist, such as ICEδ, ICEε, ICH-$1_S$ and Mch2β, which function to inhibit apoptosis. These alternative forms essentially act as dominant negative mutations and therefore are considered to be cell survival polypeptides.

The invention provides a single-well, microscale method of determining the specific apoptotic activity of a cell. The method consists of contacting a cell population of about $1 \times 10^5$ cells for a time period of between about 30 minutes and 4 hours with a sufficient volume of medium containing an apoptotic specific diagnostic reagent and a diagnostic accessory reagent so as to cover the cell population, and determining the activity of said apoptotic specific diagnostic reagent.

The method of the invention provides significant advantages over methods known in the art in that it is rapid, efficient and is specific for apoptosis. The speed and efficiency are attributed at least to the requirement of all steps being carried out without removing cells from a single microwell for the measurement of apoptotic activity. Specificity can be attributed at least to the measurement of apoptotis-specific biochemical events.

In regard to the speed and efficiency, separate procedures are not required for cell lysis and assay conditions. Moreover, following the appropriate incubation time for specific apoptotic events to occur, the method is absent of further washing procedures, transfers to additional containers and/or subsequent manipulations required for independent measurement procedures. Thus, the method of the invention essentially takes a sample of cells and adds a single solution which contains all reagents necessary for the specific detection of apoptosis, incubates the mixture and then measures the apoptotic activity within the mixture.

Apoptosis can be measured in a variety of cell types, sources and formats. Usually the cell sample will be, for example, a eukaryotic cell line or other culturable cell type and is plated into a tissue culture dish or multiwell plate treated or untreated to allow analysis of the cell sample. The cell sample can be, for example, an adherent cell type or one which grows in suspension. Other types of cell samples such as tissues are similarly amenable for use in the method of the invention. Those skilled in the art will know, or can determine, the appropriate conditions which are necessary to enable practicing of the method on various types of cell samples.

The cell number utilized in the methods of the invention can be varied depending on the cell type and which diagnostic reagent will be used to determine specific apoptotic activity of the cell. For example, the Jurkat T-cell line expresses relatively high levels of caspase activity and fewer than 100,000 cells are required to obtain an accurate measurement. Cells which express lower levels of caspase activity compared to the Jurkat line can also be used. However, a larger cell population will necessarily be employed. Those skilled in the art will know or can determine the relative levels of caspase activity in a particular cell sample and will therefore know the quantity of cells required for determining specific apoptotic activity.

Therefore, the invention provides the measurement of specific apoptotic activity in a cell population with as few as 10,000 and as many as $1\times10^6$ cells. Usually the call population is greater than about 50,000 to allow for relatively simple detection and preferably the cell population is about 100,000. Of course, the cell population can be further decreased compared to those sizes given above, and the method can be compensated for by allowing a slightly longer incubation time with the apoptotic stimulus, detection reagent and/or both. Thus, there are a variety of alternatives available to those skilled in the art which can be employed to practice the invention.

Reagents necessary for apoptosis include an apoptotic specific diagnostic reagent and an accessory reagent. The diagnostic reagent will vary depending on the specific apoptotic event that will be measured. For example, caspase activity can be used as a marker of specific apoptotic activity. Activity can be determined using, for example, caspase substrate analogues which contain a detectable moiety. Although a variety of different labels can be utilized for the detectable moiety, for use in the single-well method of the invention, the detectable moiety should have a different property following cleavage of substrate when compared to the starting substrate analogue. The change in properties for the label allows for measurement of specific apoptotic activity without the need for additional steps to be performed in the assay to remove, for example, unreacted or unbound substrates form products. Thus, diagnostic reagents which contain detectable moieties that fluoresce or luminesce, for example, upon cleavage are amenable for use in the single-well method of the invention. Specific examples of such caspase substrate analogues containing detectable moieties that fluoresce upon cleavage include the peptide analogues ZEVD-AMC, YVAD-AMC (SEQ ID NO;2) and DEVD-AMC (SEQ ID NO;1). Alternatively, detectable moieties which fluoresce at a different wavelength following cleavage or even following binding to a caspase are also amenable for use in the methods described herein.

Apoptotic specific diagnostic reagents other than caspase substrate s exist as well and can alternatively be used in the methods of the invention. A specific example of such other diagnostic reagents includes the phospholipid binding polypeptide Annexin V. As with the above-described caspase substrate analogues, these other diagnostic reagents can similarly be used in the methods of the invention because they measure a specific apoptotic event, or can be made to measure a specific apoptotic event, and also do not require additional procedures or manipulations in order to obtain a positive indication of apoptotic activity.

Annexin V, for example, has a high affinity for phosphatidylserine which is translocated to the outer membrane during cell death. Binding of Annexin V is therefore a measure of apoptotic activity. Phospholipid binding can be determined by, for example, FITC labeled Annexin V followed by removal of unbound label by filtration. The use of sample wells having bottoms comprising membrane filters can be used in conjunction with Annexin V as a diagnostic agent since filtration and subsequent analysis can occur without the need for sample transfer or additional processing steps. Diagnostic reagents other than Annexin V exist and are known to those skilled in the art. Such other reagents can similarly be used in the methods of the invention given the teachings provided herein.

An accessory reagent is also required for use in the claimed methods of the invention. The accessory reagent will vary depending on the type of diagnostic reagent used. For example, when using a caspase substrate analogue as the diagnostic reagent, the accessory reagent will be an agent that allows for the lysis, solubilization or permeabilization of the cell membrane. Such procedures will either liberate the cytoplasmic contents of a cell to allow for measurement of caspase activity or allow transport of the substrate analogue across the lipid bilayer. Reagents other than those that destroy or permeabilize the membrane can be employed as well so long as they allow the colocalization of the diagnostic reagent with the particular molecule or activity to be measured. For example, lipid vesicles or other delivery particles as well as receptor mediated events can similarly be used as the accessory reagent for colocalizing the diagnostic reagent with the cytoplasmic contents of an apoptotic cell.

Selection of an accessory reagents will vary depending on the particular application and/or apoptotic event that will be measured. Accessory reagents have been described above in reference to caspase activity for the measurement of cytoplasmic apoptotic events. However, alternative accessory reagents can be employed for the measurement of apoptotic events on the cell surface or cell exterior. In this regard, it is not necessary to bring together the cytoplasmic contents and the diagnostic reagent if the apoptotic event is localized on the cell surface or exterior. In this particular case, the accessory reagent can be, for example, an agent which allows for better access of the diagnostic reagent to the cell surface or exterior.

In addition, accessory reagents can also be, for example, cofactors or other compounds which enable functioning of the diagnostic reagent. For example, the diagnostic reagent Annexin V is a calcium dependent phospholipid binding polypeptide. An accessory reagent for Annexin V can therefore be the presence of calcium in the medium to facilitate binding of the diagnostic reagent with phosphatidylserine on apoptotic cells. In some instances there may not be a requirement for a reagent to facilitate measurement or colocalization of the diagnostic reagent. In these particular instances, the accessory reagent can be, for example, the buffer in which the diagnostic reagent works optimally.

Additionally, an accessory reagent can be more than one reagent present in the medium containing the diagnostic reagent. For example, an accessory reagent can have two components such as a lysis reagent and a cofactor or other agent which facilitates measurement of apoptotic activity. Moreover, reagents which enhance the specificity of the diagnostic reagent can additionally be included as an accessory reagent. Dyes which measure cell viability are specific examples of such accessory reagents which enhance specificity. Those skilled in the art will know or can determine what combinations of agents should be used as an accessory reagent. Thus, the choice of the accessory reagent will depend on the diagnostic molecule and the apoptotic event to be measured. Those skilled in the art will similarly know which accessory reagents are applicable with which diagnostic reagents given the teachings described herein.

Depending on the cell type, number and diagnostic reagent used, incubation time periods will vary according to the need and the specific apoptotic activity to be measured. For example, using Jurkat cells, and measuring for the induction of caspase activity as little as a 30 minute incubation period with the diagnostic reagent is required for detection of a signal. This period of incubation is measured after, for example, the induction of apoptosis. For the specific example, of caspase activity, enzyme production of product will increase over time and will similarly lead to an increase in signal. Therefore, longer incubation periods with the diagnostic reagent will lead to stronger signals. Other factors can be adjusted to modify the incubation time needed to determine the specific apoptotic activity of a cell. For example, cell number or reagent concentrations can be increased to decrease the incubation time necessary to obtain a reliable measurement. Such modifications are known to those skilled in the art or can be routinely determined by testing various cell numbers and reagent concentrations over several time points to determine those modifications which provide optimal performance for the particular need Normally, not more than 6 hours is required for detection of apoptotic activity, preferably between about 30 minutes and 2 hours and usually not more than about 1 hour of incubation with a diagnostic reagent is necessary for measuring the specific apoptotic activity of a cell.

As with cell type, cell number, reagent concentrations and incubation times, so can medium volumes be varied to obtain a desired result or to fit a particular need. For example, medium volumes sufficient to cover the cell sample should be used so as to allow adequate measurement of apoptotic activity. Volumes can be adjusted according to the solubility properties of the diagnostic reagent and the accessory reagent. Essentially, all that is necessary is for the medium to contain the appropriate amounts of required reagents and to make the reagents available to the molecules to be measured. Preferably the volumes should be confined to that of a microwell chamber such as a 96-well ELISA plate. Such volumes are generally between about 1 and 200 $\mu$l, more preferably between about 30 and 125 $\mu$l and preferably about 100 $\mu$l. Those skilled in the art will know what volumes are useful for the particular situation.

Thus, the method is amenable to a multiwell format assay where large numbers of samples cat be screened rapidly and efficiently. In particular, a 96 well format provides practical advantages since plates appropriate for manipulations and measuring devices are commercially available. Such procedures can be further automated to increase further the speed and efficiency of the method. These features, combined with the specificity of the method, allows for the high throughput screening of compounds which either induce or inhibit apoptosis. For example, a library of test compounds can be administered to a plurality of cell sample populations and then assayed for their ability to induce or inhibit apoptosis. Each of the different test compounds is administered for a sufficient time so as to induce or inhibit apoptosis prior to determining specific apoptosis activity. Such an incubation time is usually about 2 minutes to 4 hours. Identified compounds are valuable for both therapeutic and diagnostic purposes since they can allow for the treatment and detection of apoptotic mediated diseases. Such compounds are also valuable in research related to apoptotic mechanisms since they can help deduce further molecular events and provide further specificity for the discovery and development of future compounds.

The single-well microscale method described previously for determining the specific apoptotic activity of a cell can also be employed for the rapid screening and identification of inhibitors of apoptosis. Therefore, the invention also provides a rapid method of identifying a compound which inhibits apoptosis. The method consists of (a) separately contacting a plurality of cell populations with a different compound to be tested for apoptotic inhibiting activity; (b) incubating said cells with a direct stimulus of the cell death pathway for a period of between about 2 minutes to 3 hours, and (c) measuring the specific apoptotic activity of the cells.

The invention further provides a method of identifying a compound which induces apoptosis. The method consists of (a) providing a cell overexpressing a cell survival polypeptide, the cell survival polypeptide being overexpressed at a level which is sufficient to prevent the induction of apoptosis; (b) treating the cell overexpressing the cell survival polypeptide with a direct stimulus of the cell death pathway; (c) adding a compound to be tested for apoptotic inducing activity, and (d) determining cellular apoptotic activity, wherein the presence of apoptotic activity is indicative of the compound being an apoptotic inducer.

The method described above for the identification of inducers of apoptosis is particularly valuable providing an enhanced format for measuring apoptotic activity in that a cell is treated so that it is "poised" for programmed cell death. In this way the cell has synthesized and/or activated all necessary components that are required for programmed cell death. All that is necessary is a stimulus to push the cell past its holding point and into apoptosis. A positive test compound in just that stimulus to cause the cell to progress into programmed cell death.

The holding point which prevents the cell from proceeding into programmed cell death is the overexpression of a cell survival polypeptide. Cell survival polypeptides are characterized in that they exhibit the ability to prevent apoptosis when expressed or activated in a cell induced to undergo apoptosis. For example, in the absence of a functioning cell survival polypeptide, a cell treated with an apoptotic inducer will initiate the programmed cell death pathway and eventually die by apoptosis. However, in the presence of a cell survival polypeptide, treatment with an apoptotic inducer can initiate the programmed cell death pathway but the cell will survive due to inhibition of one or more events along the pathway. Depending upon the point at which the cell survival polypeptide functions, the programmed cell death pathway can be inhibited early or relatively late within the execution of the cascade of events leading to ultimate cell death. Cell survival polypeptides and their encoding nucleic acids are well known in the art and include, for example, the Bcl-2 family of related proteins Bcl-2, Bcl-xL, Mcl-1, ElB-19K as well as inhibitors of the caspases such as p35, crmA and the dominant-negative forms of the caspases. These forms include, for example, caspase's with an inactivating mutation of the active site cysteine.

Overexpression of a cell survival polypeptide can be achieved using, for example, recombinant methods known to those skilled in the art. Routine procedures for performing such recombinant expression methods are described in, for example, Sambrook et al., *Molecular Cloning: A Laboratory Manual*, Cold Spring Harbor Laboratory, New York (1992), and in Ansubel et al., *Current Protocols in Molecular Biology*, John Whiley and Sons, Baltimore, Md. (1989). Such methods can be used to express stably or transiently a cell survival polypeptide at a level which is sufficient to prevent the induction of apoptosis. The nucleic acid encoding the cell survival polypeptide can be encoded by, for example, a homologous nucleic acid derived from the same species or cell type, or alternatively, it can be encoded by a heterologous nucleic acid derived from a different species or cell type. The source of the encoding nucleic acid is not important so long as the encoded cell survival polypeptide exhibits apoptosis inhibiting activity.

A level of expression of a cell survival polypeptide which is sufficient to prevent the induction of apoptosis is known to those skilled in the art and can also be routinely determined by those skilled in the art. Expression vectors and systems are known and commercially available which provide for recombinant polypeptide expression. It is a routine matter for one skilled in the art to choose a vector or system which will provide sufficient levels of expression in a particular host cell. Alternatively, the expression level sufficient to prevent the induction of apoptosis can be routinely determined by expressing the cell survival polypeptide and then measuring whether the cell survives after treatment with an apoptotic stimulus.

In addition to recombinant methods of overexpressing a cell survival polypeptide, a cell can be used which inherently over expresses a cell survival polypeptide. A specific example of a cell inherently overexpressing a cell survival polypeptide is the B cell lymphoma in which Bcl-2 was initially identified. This leukemia has a translocation of chromosome 14 to 18 causing high level expression of Bcl-2 and therefore cell survival. The leukemic phenotype is due to the increased cell survival. Other cell lines which inherently overexpress a cell survival polypeptide, either by natural or unnatural mechanisms, exist and can similarly be used in the methods of the invention.

The block from apoptosis due to overexpression of a cell survival polypeptide and the treatment of the cells with a direct stimulus of apoptosis provide antagonistic influences to the cell. In this way, the cells are then essentially poised for programmed cell death. A direct stimulus for apoptosis can be a variety of different insults to the cell including, molecular, environmental and physical stimuli. As defined previously, such stimuli are known to those skilled in the art and can be characterized by activating a molecule within the apoptotic pathway. Examples of direct stimuli of apoptosis include inducers such as Fas ligand, anti-Fas antibody, Staurosporine, ultraviolet and gamma irradiation. Thus, treatment of a cell over expressing a cell survival polypeptide with a direct stimulus of apoptosis will prime the cell for apoptosis since both positive and negative signals are providing balancing effects. One advantage of this priming is that all cell death components are available for apoptosis once a signal is received that overrides the block of the cell survival polypeptide. This advantage allows for the rapid induction of apoptosis which can be beneficial when used to screen for compounds that possess apoptosis inducing activity when Bcl-2 or Bcl-xL is the cell survival polypeptide. Such cells are particularly useful in screening for inhibitors of Bcl-2 or Bcl-xL, respectively.

In addition to treating the cells with a direct stimulus of apoptosis, the cells are also treated with one or more compounds which are to be tested for apoptosis inducing activity. The compounds can be, for example, small molecules, peptides, polypeptides, proteins or other macromolecules. Essentially, the type of compound which is to be tested is unimportant, only that the user desires to test whether the compound has apoptotic inducing activity. Therefore, the assay is applicable for a variety of different settings, including clinical, diagnostic and drug discovery.

Although essentially any method which distinguishes apoptosis from necrosis, for example, can be used to determine cellular apoptotic activity, the use of the single-well method described previously for measuring apoptotic activity provides advantages. This method allows for the rapid and efficient determination of apoptosis in what can be utilized in a multiwell or high throughput format. Therefore, once the compounds are administered to the cell, apoptotic activity of the cell is determined by, for example, the rapid measurement of caspase activity, or alternatively any of a variety of other methods known in the art. Those samples which yield positive results compared to control samples are indicative of compounds which will induce programmed cell death.

It is understood that modifications which do not substantially affect the activity of the various embodiments of this invention are also included within the definition of the invention provided herein. Accordingly, the following examples are intended to illustrate but not limit the present invention.

EXAMPLE I

Measurement of Specific Apoptotic Activity

This Example describes the use and characteristics of the single-well method for the measurement of specific apoptotic activity and screening of compound libraries for inducers of apoptosis.

A human T cell leukemia clonal (Jurkat) cell line was used below for demonstrating and characterizing the single-well method for measuring specific apoptotic activity of a cell. For the screening of compounds, this Jurkat cell line was stably transfected with an expression construct for the cell survival polypeptide Bcl-2 and clonal cell lines were generated from the stable transfectants. The cell lines were constructed using methods known in the art and essentially as described in Sambrook et al., *Molecular Cloning: A Laboratory Manual*, Cold spring Harbor Laboratory, New York (1992). Cell lines were cultured in RPMI 1640 and 10% fetal bovine serum (FBS), in the presence of a maintenance level of G418 (200 μg/ml). A neo-transfected cell line was constructed and cultured in a similar way for use as a control.

To ensure that the transfected cell lines were expressing Bcl-2, cell lysates were prepared from positive clones and Bcl-2 levels were measured by polypeptide blot analysis. Briefly, cell lysates were prepared from 500,000 transfectants by first pelleting the culture and then solubilizing the cells in mercaptoethanol-SDS buffer (5% (w/v) sodium dodecyl sulphate, 15% (v/v) glycerol, 0.01% (w/v) bromophenol blue, 10% (v/v) β-mercaptoethanol in 250 mM Tris-HCl, pH6.0). Polypeptides within the lysate were separated by SDS-polyacrylamide gel electrophoresis and transferred to nitrocellulose by electro-blotting. Detection was performed using a Bcl-2 specific monoclonal antibody that recognizes both endogenous and transfected forms of Bcl-2 (Hockenbery et al., *Nature* 348:334–336 (1990)). Expression levels were quantified by using different amounts of purified recombinant Bcl-2 run on the same gel as a comparison. Comparison of the transfected Bcl-2 expression levels with the known amounts indicated an expression level of about 6 ng/$10^6$ cells. The expression level of endogenous Bax, detected with an anti-Bax specific antibody and quantified in a similar manner was determined to be about 1 ng/$10^6$ cells (Reed et al., *Analytical Biochem.* 205:70–76 (1992)).

To induce apoptosis, either a neo-transfected Jurkat cell line or the above Bcl-2 transfected cell line was used. Specifically, the cell lines were harvested, washed in RPMI 1640 (without phenol red as an indicator) and 10% FBS, and resuspended at a density of 1.33×10⁶ cells/ml in the same medium. Cells were plated in 96-well plates at 100,000 cells/well in a 75 μl volume and allowed to acclimatise for 1 hour at 37° C. Apoptosis was induced by incubation with an anti-Fas antibody which was added to the cells to a final concentration of 100 ng/ml and allowed to incubate for 3 hours at 37° C. (11 μl of a 10× stock solution; MBL, Pavera: Madison, Wis.; Yonehara et al., *Experimental Med.* 169:1747–1756 (1989)). Alternatively, for screening procedures, compounds were pre-incubated with the Bcl-2 transfected cells for 1 hour at 37° C. prior to the addition of anti-Fas antibody. Compounds to be tested were added to duplicate wells at a 4× concentration (25 μl) resulting in a final concentration of 5 μg/ml compound and 1% DMSO.

Apoptosis was determined by measuring aspartic specific cysteine protease (caspase) activity following anti-Fas antibody incubation. Briefly, the cells were lysed by the addition of 10× lysis buffer and shaking in an orbital shaker for 5 min at room temperature (12.3 μl/well; 2 mM PMSF, 10 mM DTT, 10 μg/ml Pepstatin A, 10 μg/ml Leupeptin, 50 μg/ml Aprotenin, 1 mM EDTA, 1 mM EGTA and 5% CHAPS in 10× hypotonic buffer (100 mM Hepes pH 7.4, 420 mM KCl, 50 mM $MgCl_2$)). ICE buffer was subsequently added (70 μl/well of a 2× stock prepared as follows: 40 mM Hepes, pH 7.5, 2 mM EDTA, 20% Sucrose and 0.2% CHAPS to which DTT was added fresh before the start of every assay to a final concentration of 10 mM) and the enzyme assay was initiated by addition of the DEVD-AMC substrate to a final 2 μM concentration (10 μl of a 20× stock). Alternatively, the lysis buffer, ICE buffer and DEVD-AMC substrate can be combined into a single buffer and added in one step. Substrate cleavage activity was measured at thirty minute intervals over a period of two hours beginning at time zero in a fluorescent plate reader. The excitation wavelength was 360/40 nm and the emission wavelength 460/40 nm.

Controls run on each multiwell plate included a matching neo-transfected cell line treated with anti-Fas antibody, but no compound, as the positive death control and Bcl-2 transfected cells with and without antibody as the background controls.

The characterization and use of the above method for screening inducers of apoptosis is described further below.

Figure 1B:
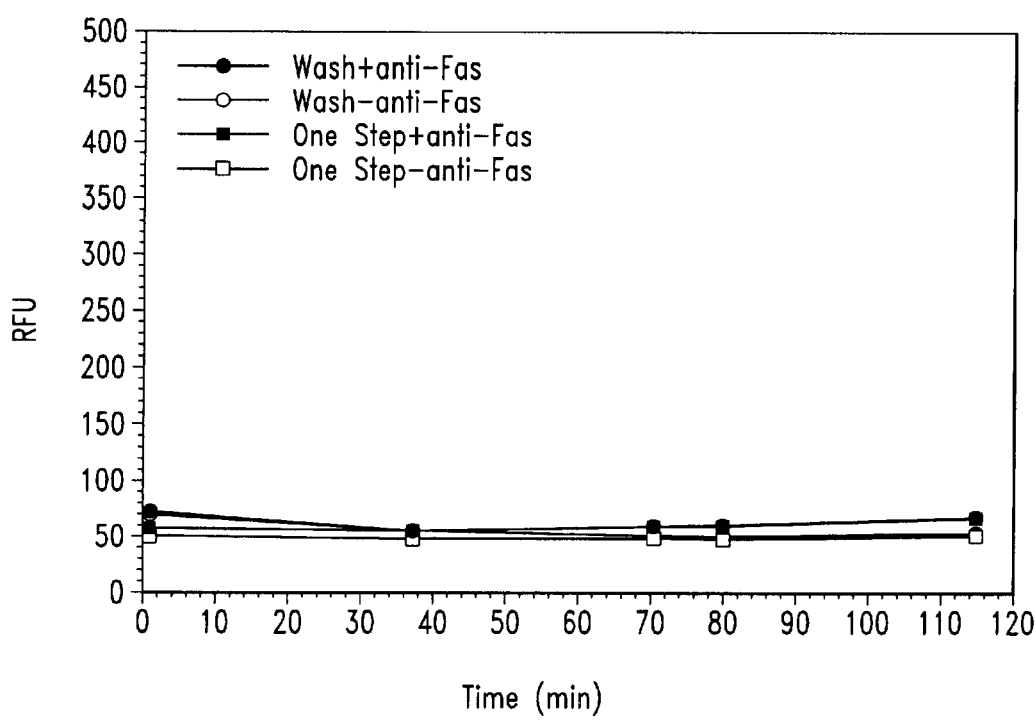
FIG. 1B shows the inhibition of induced caspase activity in Bcl-2 transfected cells in the presence or absence of anti-Fas anti-body. (●: wash+anti-Fas; ○:wash-anti-Fas; ■:single-well+anti-Fas; □: single-well-anti-Fas)

Studies were initially carried out comparing the single-well method described above (where the entire experiment is carried out in the same well), with a known method where cells are spun down and washed after anti-Fas antibody treatment and before addition of lysis buffer. This comparison is presented in FIG. 1A. The results show that both methods yield comparable caspase activity as demonstrated by the CPP32-like enzymatic cleavage of the DEVD-AMC substrate in neo-transformed cell lines. In contrast, cell lines transfected with Bcl-2 are protected from Fas induced death and show little increase in cleavage (FIG. 1B). These results demonstrate that the single-well method can accurately measure both the induction and inhibition of caspase activity at a sensitivity comparable to previously used methods.

Further characterization of the single-well method demonstrated that the presence of 10% FBS was beneficial throughout the course of the assay, up to lysis of the cells. For example, substitution with 0.5% bovine serum albumin resulted in induction of CPP32-like activity in the neo-transfected Jurkat cells in the absence of anti-Fas antibody treatment. This effect is likely due to induction of apoptosis through growth factor withdrawal. However, the expression of Bcl-2 was able to protect the cells from this effect.

Further, compounds in libraries for high throughput screening are routinely maintained as stock solutions dissolved in DMSO. Further characterization of the single-well method was carried out to determine permissible levels of DMSO permissible in the method. The results indicated that up to at least 1% DMSO had no significant effect on the cells or the accuracy of the method. Testing of the possible effect of the media component phenol red, which is normally used as an indicator in RPMI, had a slight, but significant, quenching effect on the fluorescence readings. Due to this effect, phenol red was removed from the media in all further assays.

To optimize the incubation time and concentration of anti-Fas antibody, studies were performed which measured the caspase activity over a range of incubation time points and concentration of anti-Fas antibody. Caspase activity was determined in both neo- and Bcl-2 transfected cells. In the neo-transfected cells, induction of a CPP32-like activity increased with anti-Fas antibody concentration up to 30 ng/ml, after which a plateau was reached. A slight, but significant, increase in CPP32-like activity was observed in the Bcl-2-transfected Jurkats at an antibody concentration of 100 ng/ml.

Figure 2A:
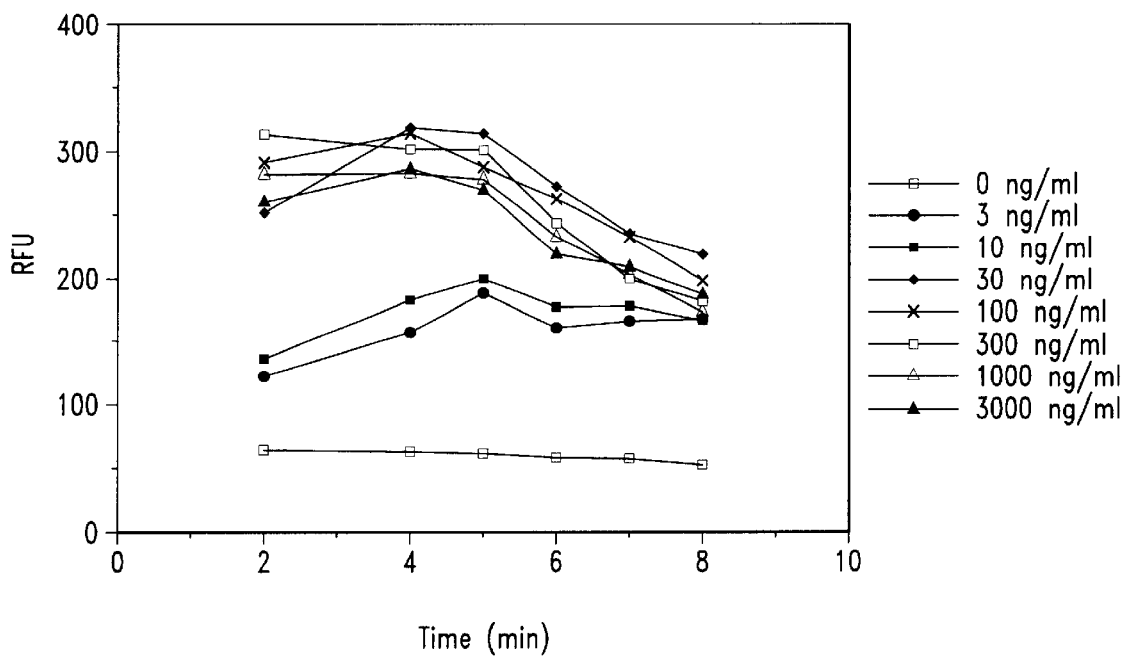
FIG. 2A shows the anti-Fas antibody titration and caspase time course in neo-transfected Jurkat cells.
Figure 2B:
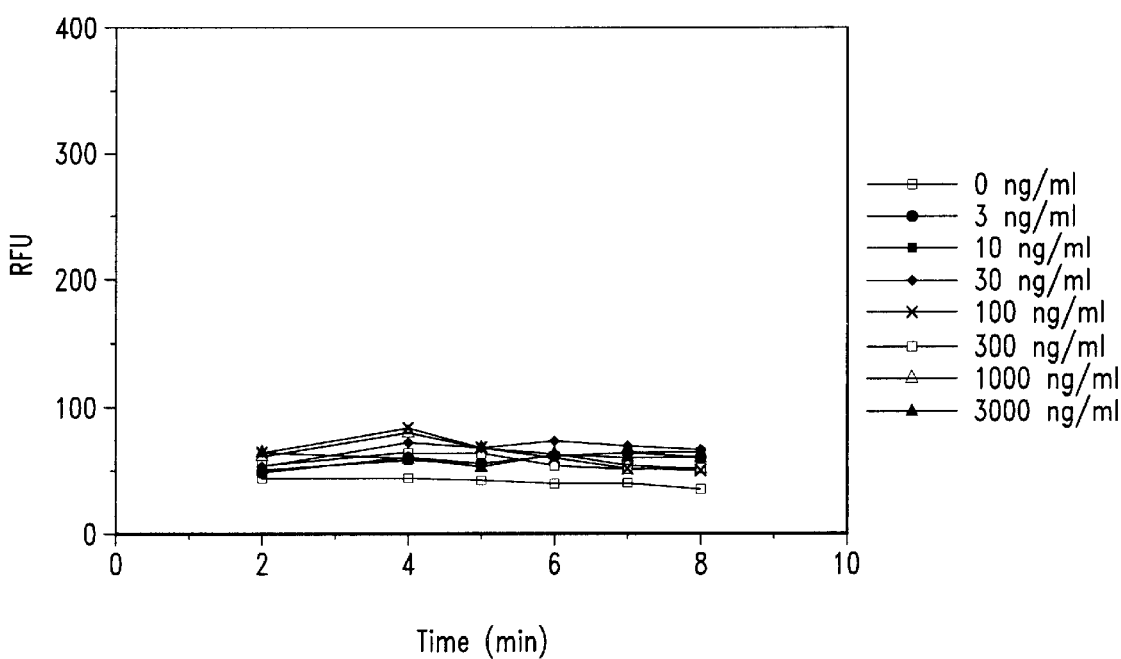
FIG. 2B shows a parallel titration and time course in Bcl-2 transfected Jurkat cells.

At anti-Fas antibody concentrations above 10 ng/ml the highest enzymatic activity was observed between 2 and 5 hours after addition of the antibody to neo-transfected Jurkat cells. Longer incubation times resulted in a decrease of observable CPP32-like activity (FIG. 2A). In Bcl-2 transfected cells, what little enzymatic activity was detected was seen only at an incubation time of 4 hours (FIG. 2B). From the above results an antibody concentration of 100 ng/ml incubated for 3 hours, was chosen as the standard running conditions for the assay.

Further characterization of the assay was performed by assessing both the intra-assay and inter-assay variation. Specifically, the intra-assay variation of the procedure was examined by running 12 wells of each of the neo-transfected and of the Bcl-2 transfected cell lines on the same plate at the same time in the presence or absence of anti-Fas antibody. The results of this study are shown in Table 1 and reveal an overall intra-assay variation of 6.8% or less of the mean of the caspase activity of the positive, neo-transfected control treated with anti-Fas.

TABLE 1

|  | Intra-assay variation (RFU) | | |
| --- | --- | --- | --- |
|  | Mean | Std Dev | % CV |
| Neo-transfected + anti-Fas antibody | 228.3 | 15.6 | 6.8 |
| Neo-transfected − anti-Fas antibody | 17.7 | 4.3 | 1.9 |
| Bcl2-transfected + anti-Fas antibody | 10.2 | 3.3 | 1.4 |
| Bcl2-transfected − anti-Fas antibody | 2.4 | 3.5 | 1.5 |

RFU = Relative Fluorescent Units
std Dev = Standard Deviation
% CV = Percent coefficient of Variation
Percent coefficient of Variation is defined as: % CV = (Standard Deviation/Mean of Neo-transfected + anti-Fas) *100

Alternatively, the inter-assay variation was determined by running each of the neo- or Bcl-2 transfected cell lines 24 on separate plates over the course of two days. Each plate was set up individually. The result of this determination are presented in Table 2 and reveal an overall inter-assay variation of 7.0% or less of the mean of the caspase activity of the positive, neo-transfected control treated with anti-Fas.

TABLE 2

|  | Inter-assay variation (RFU) | | |
| --- | --- | --- | --- |
|  | Mean | Std Dev | % CV |
| Neo-transfected + anti-Fas antibody | 221.5 | 15.5 | 7.0 |
| Neo-transfected − anti-Fas antibody | 7.7 | 2.9 | 1.3 |
| Bcl2-transfected + anti-Fas antibody | 22.4 | 8.2 | 3.7 |
| Bcl2-transfected − anti-Fas antibody | −1.5 | 2.0 | 0.9 |

RFU = Relative Fluorescent Units
Std Dev = Standard Deviation
% CV = Percent coefficient of Variation
Percent coefficient of Variation is defined as: % CV = (Standard Deviation/Mean of Neo-transfected + anti-Fas) *100

EXAMPLE II

Screening Compounds for the Induction of Apoptosis

This Example describes the use of the screening of a compound library for the detection of apoptotic inducers.

The single-well method for determining specific apoptotic activity was used in conjunction with Bcl-2 transfected cells to identify compounds that exhibit apoptotic inducing activity. The procedures and the Bcl-2 transfected cell line was described above in Example I.

Figure 3:
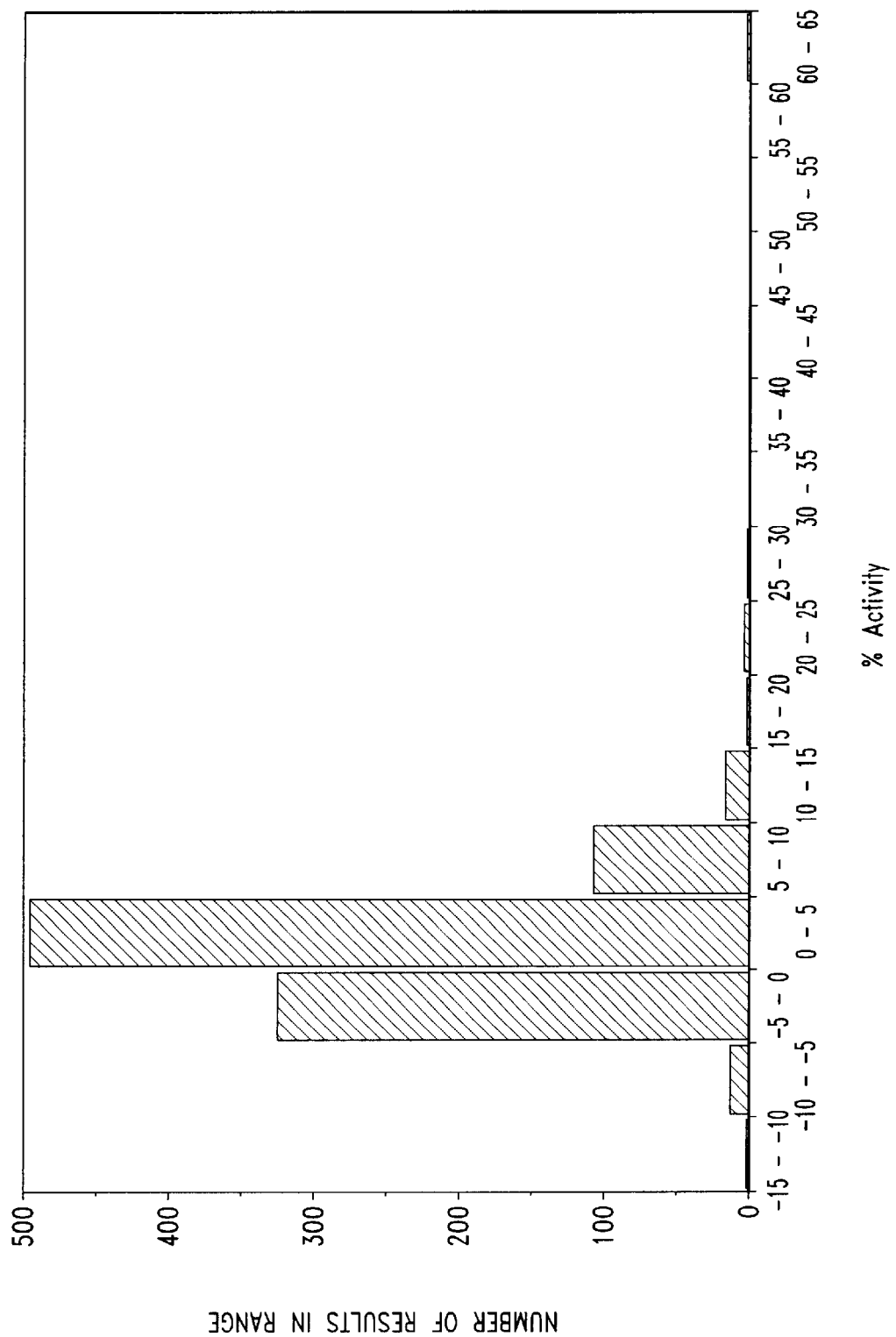
FIG. 3 shows the screening of a chemical compound library using Bcl-2 transfected cells primed with anti-Fas antibody and the identification of positive apoptotic inducers.

Briefly, 960 compounds chosen from a chemical library were examined for their ability to induce apoptosis in cells that were primed by the incubation of Bcl-2 stably transfected cells with anti-Fas antibody. The screening was performed in a multiwell or high throughput mode and the compounds were incubated at a concentration of 5 µg/ml. The results of this screen are shown in FIG. 3. Values are expressed as a percentage of caspase activity of the positive, neo-transfected control treated with anti-Fas present on each plate. The levels of caspase activity ranged from 62.1 to −11.5% of the non-Bcl-2 protected control. A mean value of 1.7% and a standard deviation of 4.2% was also observed.

The threshold for defining a compound as positive was set at 24% of the caspase activity of neo-transfectants in the absence of any compound (46 relative fluorescence units). This number was determined by the mean plus 3 standard deviations of the negative controls (anti-Pas treated Bcl-2-transfected cells) shown in Table 2 for calculating the inter-assay variation. This threshold is valid assuming a normal distribution for the results. Given this assumption, the probability that a negative compound will exceed the mean of the negative controls by more than 3 standard deviations is 0.0028. Using this criterion, 5 positives were identified from the 960 compounds screened.

Throughout this application various publications have been referenced. The disclosures of these publications in their entireties are hereby incorporated by reference in this application in order to describe more fully the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:

1. A method of identifying a compound which induces apoptosis comprising:
    (a) providing a cell overexpressing a cell survival polypeptide, said cell survival polypeptide being overexpressed at a level which is sufficient to prevent the induction of apoptosis upon treatment with a stimulus of step (b), wherein said cell survival polypeptide comprises Bcl-2, Bcl-xL, Mcl-1 or E1B-19K;
    (b) treating said cell overexpressing said cell survival polypeptide with a direct stimulus of the cell death pathway;
    (c) adding a compound to be tested for apoptosis inducing activity, and determining cellular apoptotic activity, wherein the presence of apoptotic activity is indicative of said compound being an apoptotic inducer.

2. The method of claim 1, wherein said cell survival polypeptide is overexpressed at a level so as to prevent the induction of a direct stimulus of the cell death pathway.

3. The method of claim 2, wherein said cell survival polypeptide is overexpressed at a level so as to prevent the induction of apoptosis by a direct stimulus selected from the group consisting of Fas ligand, anti-Fas antibody, staurosporine, UV and gamma irradiation.

4. The method of claim 1, wherein said direct stimulus of the cell death pathway is selected from the group consisting of Fas ligand, anti-Fas antibody, staurosporine, UV and gamma irradiation.

5. The method of claim 1, wherein said cell survival polypeptide is encoded by an exogenous nucleic acid.

6. The method of claim 5, wherein said exogenous nucleic acid is a homologous nucleic acid.

7. The method of claim 5, wherein said exogenous nucleic acid is a heterologous nucleic acid.

8. The method of claim 1, wherein said compound tested for apoptotic inducing activity further comprises a compound which inhibits the activity of a cell survival polypeptide.

9. The method of claim 1, wherein determining apoptotic activity further comprises lysing said cells and determining the caspase activity in said lysate.

10. The method of claim 1, wherein determining apoptotic activity further comprises contacting the cells with Annexin 5 and determining the amount of Annexin 5 which binds.

11. The method of claim 1, wherein said cell survival polypeptide is encoded by an endogenous nucleic.

12. The method of claim 1, wherein said compound tested for apoptotic inducing activity further comprises a compound which induces caspase activity in a cell.

13. The method of claim 1, wherein said compound tested for apoptotic inducing activity further comprises a compound which promotes the activity of a cell death polypeptide.

14. A method of identifying a compound which induces apoptosis comprising:
    (a) providing a cell overexpressing a cell survival polypeptide, said cell survival polypeptide being overexpressed at a level which is sufficient to prevent the induction of apoptosis upon treatment with a stimulus of step (b), wherein said cell survival polypeptide is encoded by an endogenous nucleic acid;
    (b) treating said cell overexpressing said cell survival polypeptide with a direct stimulus of the cell death pathway;
    (c) adding a compound to be tested for apoptosis inducing activity, and determining cellular apoptotic activity, wherein the presence of apoptotic activity is indicative of said compound being an apoptotic inducer.

15. The method of claim 14, wherein said cell survival polypeptide is overexpressed at a level so as to prevent the induction of a direct stimulus of the cell death pathway.

16. The method of claim 15, wherein said cell survival polypeptide is overexpressed at a level so as to prevent the induction of apoptosis by a direct stimulus selected from the group consisting of Fas ligand, anti-Fas antibody, staurosporine, UV and gamma irradiation.

17. The method of claim 14, wherein said direct stimulus of the cell death pathway is selected from the group consisting of Fas ligand, anti-Fas antibody, staurosporine, UV and gamma irradiation.

18. The method of claim 14, wherein said compound tested for apoptotic inducing activity fierier comprises a compound which induces caspase activity in a cell.

19. The method of claim 14, wherein said compound tested for apoptotic inducing activity further comprises a compound which inhibits the activity of a cell survival polypeptide.

20. The method of claim 14, wherein said compound tested for apoptotic inducing activity further comprises a compound which promotes the activity of a cell death polypeptide.

21. The method of claim 14, wherein determining apoptotic activity further comprises lysing said cells and determining the caspase activity in said lysate.

22. The method of claim 14, wherein determining apoptotic activity further comprises contacting the cells with Annexin 5 and determining the amount of Annexin 5 which binds.

23. A method of identifying a compound which induces apoptosis comprising:
  (a) providing a cell overexpressing a cell survival polypeptide, said cell survival polypeptide being overexpressed at a level which is sufficient to prevent the induction of apoptosis upon treatment with a stimulus of step (b);
  (b) treating said cell overexpressing said cell survival polypeptide with a direct stimulus of the cell death pathway;
  (c) adding a compound to be tested for apoptosis inducing activity, and determining cellular apoptotic activity, wherein the presence of apoptotic activity is indicative of said compound being an apoptotic inducer, wherein said compound tested for apoptotic inducing activity further comprises a compound which induces caspase activity in a cell.

24. A method of identifying a compound which induces apoptosis comprising:
  (a) providing a cell overexpressing a cell survival polypeptide, said cell survival polypeptide being overexpressed at a level which is sufficient to prevent the induction of apoptosis upon treatment with a stimulus of step (b);
  (b) treating said cell overexpressing said cell survival polypeptide with a direct stimulus of the cell death pathway;
  (c) adding a compound to be tested for apoptosis inducing activity, and determining cellular apoptotic activity, wherein the presence of apoptotic activity is indicative of said compound being an apoptotic inducer, wherein said compound tested for apoptotic inducing activity further comprises a compound which promotes the activity of a cell death polypeptide.

25. The method of claim 23 or 24, wherein said cell survival polypeptide is overexpressed at a level so as to prevent the induction of a direct stimulus of the cell death pathway.

26. The method of claim 25, wherein said cell survival polypeptide is overexpressed at a level so as to prevent the induction of apoptosis by a direct stimulus selected from the group consisting of Fas ligand, anti-Fas antibody, staurosporine, UV and gamma irradiation.

27. The method of claim 23 or 24, wherein said direct stimulus of the cell death pathway is selected from the group consisting of Fas ligand, anti-Fas antibody, staurosporine, UV and gamma irradiation.

28. The method of claim 23 or 24, wherein said cell survival polypeptide is encoded by an exogenous nucleic acid.

29. The method of claim 28, wherein said exogenous nucleic acid is either a homologous or heterologous nucleic acid.

30. The method of claim 28, wherein said exogenous nucleic acid is a heterologous nucleic acid.

31. The method of claim 23 or 24, wherein determining apoptotic activity further comprises lysing said cells and determining the caspase activity in said lysate.

32. The method of claim 23 or 24, wherein determining apoptotic activity further comprises contacting the cells with Annexin 5 and determining the amount of Annexin 5 which binds.

* * * * *

UNITED STATES PATENT AND TRADEMARK OFFICE
CERTIFICATE OF CORRECTION

PATENT NO.   : 6,518,032 B1  
DATED        : February 11, 2003  
INVENTOR(S)  : Lawrence C. Fritz et al.

It is certified that error appears in the above-identified patent and that said Letters Patent is hereby corrected as shown below:

Column 21,
Line 8, "inducing activity fierier" should read -- inducing activity further --.

Signed and Sealed this

Twenty-second Day of April, 2003

JAMES E. ROGAN
*Director of the United States Patent and Trademark Office*